(12) United States Patent
Petcavich (10) Patent No.: US 12,083,116 B2
(45) Date of Patent: Sep. 10, 2024

(54) METHOD OF INDUCING DENDRITIC AND SYNAPTIC GENESIS IN NEURODEGENERATIVE CHRONIC DISEASES

(71) Applicant: Robert John Petcavich, The Woodlands, TX (US)

(72) Inventor: Robert John Petcavich, The Woodlands, TX (US)

( * ) Notice: Subject to any disclaimer, the term of this patent is extended or adjusted under 35 U.S.C. 154(b) by 774 days.

(21) Appl. No.: 17/254,534

(22) PCT Filed: Jun. 21, 2019

(86) PCT No.: PCT/US2019/038486
§ 371 (c)(1),
(2) Date: Dec. 21, 2020

(87) PCT Pub. No.: WO2019/246532
PCT Pub. Date: Dec. 26, 2019

(65) Prior Publication Data
US 2021/0267966 A1     Sep. 2, 2021

Related U.S. Application Data

(60) Provisional application No. 62/687,825, filed on Jun. 21, 2018.

(51) Int. Cl.
| | | |
|---|---|---|
| *A61K 31/48* | (2006.01) |
| *A61K 9/00* | (2006.01) |
| *A61K 9/70* | (2006.01) |
| *A61K 31/05* | (2006.01) |
| *A61K 31/12* | (2006.01) |
| *A61K 31/137* | (2006.01) |
| *A61K 31/15* | (2006.01) |
| *A61K 31/155* | (2006.01) |
| *A61K 31/352* | (2006.01) |
| *A61K 31/353* | (2006.01) |
| *A61K 31/355* | (2006.01) |
| *A61K 31/36* | (2006.01) |
| *A61K 31/375* | (2006.01) |
| *A61K 31/4045* | (2006.01) |
| *A61K 31/426* | (2006.01) |
| *A61K 31/675* | (2006.01) |
| *A61K 31/706* | (2006.01) |
| *A61K 45/06* | (2006.01) |
| *A61P 25/28* | (2006.01) |

(52) U.S. Cl.
CPC ............ *A61K 31/48* (2013.01); *A61K 9/006* (2013.01); *A61K 9/7007* (2013.01); *A61K 31/05* (2013.01); *A61K 31/12* (2013.01); *A61K 31/137* (2013.01); *A61K 31/15* (2013.01); *A61K 31/155* (2013.01); *A61K 31/352* (2013.01); *A61K 31/353* (2013.01); *A61K 31/355* (2013.01); *A61K 31/36* (2013.01); *A61K 31/375* (2013.01); *A61K 31/4045* (2013.01); *A61K 31/426* (2013.01); *A61K 31/675* (2013.01); *A61K 31/706* (2013.01); *A61K 45/06* (2013.01); *A61P 25/28* (2018.01)

(58) Field of Classification Search
CPC ...... A61K 31/48; A61K 9/006; A61K 9/7007; A61K 31/05; A61K 31/12; A61K 31/137; A61K 31/15; A61K 31/155; A61K 31/352; A61K 31/353; A61K 31/355; A61K 31/36; A61K 31/375; A61K 31/4045; A61K 31/426; A61K 31/675; A61K 31/706; A61K 45/06; A61P 25/28
USPC .......................................................... 514/52
See application file for complete search history.

(56) References Cited

U.S. PATENT DOCUMENTS

| | | | |
|---|---|---|---|
| 2018/0021326 A1* | 1/2018 | Stamets | A61K 31/4045 424/195.15 |
| 2018/0036303 A1* | 2/2018 | Raz | A61K 45/06 |

FOREIGN PATENT DOCUMENTS

WO    WO 2019/064031    *    4/2019

\* cited by examiner

*Primary Examiner* — Yih-Horng Shiao
(74) *Attorney, Agent, or Firm* — Feeney IP Law; Alan F. Feeney; Daniel Sullivan (57) ABSTRACT

The present invention discloses a method to recover and restore dendritic and synaptic neuron connections that have been degraded or destroyed by neurodegenerative diseases. In the present invention tryptamines are used to induce neuro plasticity and restore both dendritic density and synaptic connections of neurons in the brain. In the preferred embodiment LSD given in micro doses can induce dendritic and synaptic genesis in neuronal networks and improve the quality of life of people with neurodegenerative diseases such as Alzheimer's, Huntington's, Multiple Sclerosis, Parkinson's and Frontotemporal dementia.

3 Claims, 2 Drawing Sheets

Specification includes a Sequence Listing.

METHOD OF INDUCING DENDRITIC AND SYNAPTIC GENESIS IN NEURODEGENERATIVE CHRONIC DISEASES

CROSS-REFERENCE TO RELATED APPLICATIONS

This application is a continuation under 35 U.S.C. § 371 of International Application No. PCT/US2019/038486 filed on Jun. 21, 2019 that claims priority to U.S. Provisional Patent Application No. 62/687,825 filed on Jun. 21, 2018. The entire contents thereof is incorporated by reference herein.

BACKGROUND OF THE INVENTION

During the past 20 to 30 years a significant amount of research has been conducted on neurodegenerative diseases. As the population has aged worldwide, debilitating neurological disease such as Alzheimer's, Parkinson's, Frontotemporal Dementia and others have caused a significant emotional and financial burdens on developed and developing societies. As the world population ages, these afflictions will only increase and tax the current medical infrastructure to the breaking point. A solution is desperately needed to not only reduce the financial costs, but also enhance the quality of life for the millions of patients afflicted with these terrible chronic conditions.

Senile dementia has a tendency to increase with the shift to an aging society. This tendency has become a major large social problem. Dementia syndromes such as Frontal Temporal Dementia (FTD) and Alzheimer disease (AD) have their own pathologic characteristics including degeneration and loss of synaptic connections and neurons in certain brain areas, such as the cortical and cholinergic neurons.

Alzheimer's disease (AD) affects 5% of people over age 65 years, and its prevalence is increasing. Although AD manifests amyloid plaques and tau tangles, loss of synapses, eventually accompanied by neuronal loss, more closely correlates with cognitive decline. Damage to neurons occurs at least partially through generation of oxidative and nitrosative stress, due to excessive generation of reactive oxygen/nitrogen species (ROS/RNS) triggered by oligomeric amyloid-β (Aβ) peptide.

Alzheimer's disease (AD) is a chronic neurodegenerative disease that usually starts slowly and worsens over time. It is the cause of 60-70% of cases of dementia. The most common early symptom is difficulty in remembering recent events (short-term memory loss). As the disease advances, symptoms can include problems with language, disorientation (including easily getting lost), mood swings, loss of motivation, not managing selfcare, and behavioral issues. As a person's condition declines, they often withdraw from family and society. Gradually, bodily functions are lost, ultimately leading to death. Although the speed of progression can vary, the typical life expectancy following diagnosis is three to nine years.

The cause of Alzheimer's disease (AD) is poorly understood. About 70% of the risk is believed to be genetic with many genes usually involved. Other risk factors include a history of head injuries, depression, or hypertension. The disease process is associated with plaques and tangles in the brain. A probable diagnosis is based on the history of the illness and cognitive testing with medical imaging and blood tests to rule out other possible causes. Initial symptoms are often mistaken for normal ageing. Examination of brain tissue is needed for a definite diagnosis. Mental and physical exercise, and avoiding obesity may decrease the risk of AD; however, evidence to support these recommendations is not strong. There are currently no medications or supplements that have been shown to decrease risk.

No treatments stop or reverse the progression of Alzheimer's disease (AD), although some may temporarily improve symptoms. Affected people increasingly rely on others for assistance, often placing a burden on the caregiver; the pressures can include social, psychological, physical, and economic elements. Exercise programs may be beneficial with respect to activities of daily living and can potentially improve outcomes. Behavioral problems or psychosis due to dementia are often treated with antipsychotics, but this is not usually recommended, as there is little benefit with an increased risk of early death.

During the 2002 to 2012 observation period, 413 Alzheimer's disease (AD) trials were performed: 124 Phase 1 trials, 206 Phase 2 trials, and 83 Phase 3 trials. Seventy-eight percent were sponsored by pharmaceutical companies. The United States of America (U.S.) remains the single world region with the greatest number of trials; cumulatively, more non-U.S. than U.S. trials are performed. The largest number of registered trials addressed symptomatic agents aimed at improving cognition (36.6%), followed by trials of disease-modifying small molecules (35.1%) and trials of disease-modifying immunotherapies (18%). The mean length of trials increases from Phase 2 to Phase 3, and the number of participants in trials increases between Phase 2 and Phase 3. Trials of disease-modifying agents are larger and longer than those for symptomatic agents. A very high attrition rate was found, with an overall success rate during the 2002 to 2012 period of 0.4% (99.6% failure).

In 2015, there were approximately 29.8 million people worldwide with Alzheimer's disease (AD). It most often begins in people over 65 years of age, although 4% to 5% of cases are early-onset Alzheimer's which begin before this. It affects about 6% of people 65 years and older. In 2015, dementia resulted in about 1.9 million deaths. It was first described by, and later named after, German psychiatrist and pathologist Alois Alzheimer in 1906. In developed countries, AD is one of the most financially costly diseases.

Therefore, it is obvious based on all the clinical trial failures of the past that a different strategy is needed to combat such insidious disease such as Alzheimer's disease (AD). Since none of the prior therapeutic strategies has worked, it is time for a novel approach to treat chronic neurodegenerative diseases as disclosed in the present invention which is to restore both dendritic and synaptic connections in patients with non-addictive tryptamine molecules.

SUMMARY OF THE INVENTION

The object of the present invention is to restore and regenerate neuron dendritic density and synaptic connections in humans with the application of tryptamine molecules.

Another object of the present invention is to restore and regenerate neuron dendritic and synaptic connections in humans with appropriate doses of the tryptamine lysergic acid (otherwise known as Lysergic acid diethylamide or LSD).

Another object of the present invention is to restore and regenerate neuron dendritic and synaptic connections in humans with appropriate doses of the tryptamines and phenethylamines selected from the group, N, N-dimethyltryptamine, 5-methoxy-N, N-dimethyltryptamine, mescaline, psilocin, 3,4-methylenedioxymethamphetamine, and psilocybin.

These and other objects of the invention will be elucidated in the detailed description of the invention.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

Within the framework of the present description and in the subsequent claims, except where otherwise indicated, all numbers expressing amounts, quantities, percentages, and so forth, are to be understood as being preceded in all instances by the term "about". As used herein, the term "about" is defined as +5%. Also, all ranges of numerical entities include all the possible combinations of the maximum and minimum numerical values and all the possible intermediate ranges therein, in addition to those specifically indicated hereafter.

The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B and C as components.

The term "active form" or "active agent" herein refers to the metabolite form of the inactive prodrug that is metabolized within the body into its active form, regardless of the source of said prodrug.

The term "pharmaceutically acceptable salts or derivatives" herein refers to those salts or derivatives which possess the biological effectiveness and properties of the salified or derivatized compound and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate; hydrogen sulphate; citrate, maleate, fumarate, tifluoroacetate, 2-naphthalenesulphonate, and para-toluenesulphonate. Further information on pharmaceutically acceptable salts can be found in Handbook of pharmaceutical salts, P. Stahl, C. Wermuth, WILEY-VCH, 127-133, 2008, herein incorporated by reference. The pharmaceutically acceptable derivatives include the esters, the ethers and the N-oxides.

DETAILED DESCRIPTION OF THE INVENTION

Figure 1:
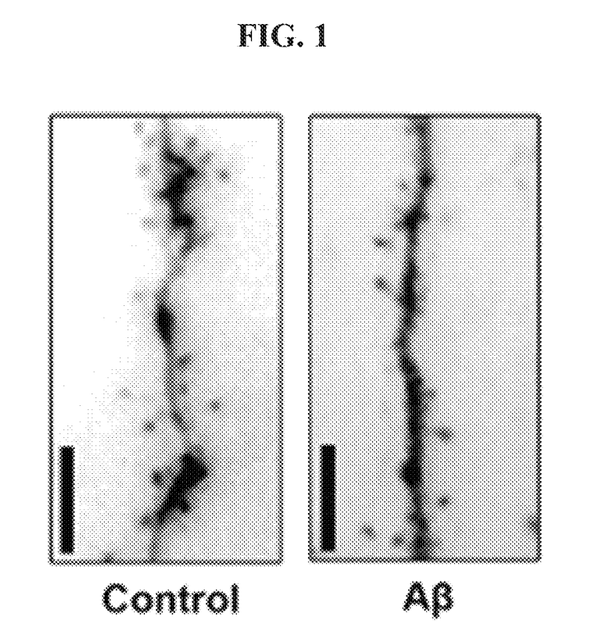
FIG. 1 shows an image of rat neurons, dendrites and synaptic connections that have been compromised by a neurodegenerative disease toxic Aβ protein.

Referring to FIG. 1, this shows scanning electron microscope (SEM) images of rat neurons the black bar represents 5-micron scale. The control sample shows neurons of healthy rats before exposure to toxic Aβ42 amyloid proteins. At this resolution one can see copious dendritic structure's, the round dark circles. The resolution is not high enough to visualize synaptic connections. The image labeled Aβ is of rat neurons after exposure for 4 days to 250 micro molar concentrations of toxic peptide. As can be seen in the image there is a significant degradation of the dendrites and although not seen the synaptic connections as well. This model emulates what is seen in the human versions of AD disease.

Autopsy results done by DeKosky et al. (Ann Neurol., 1990, 27(5):457-64) on patients that have died from Alzheimer's disease (AD) disease evidence a significant decrease in synaptic connections in their brains. The DeKosky results are summarized in Table 1 below. This is consistent with other publications showing that the number of neurons lost in AD patients at death is between 40 to 80%.

TABLE 1

|  | Control Samples | Biopsy AD Specimens | Autopsy AD Specimens |
| --- | --- | --- | --- |
| Synapses/mm$^3$ × 10$^8$ | 3.81 ± 0.2 | 2.48 ± 0.16 − 35%$^a$ | 2.22 ± 0.12 − 42%$^a$ |
| Length of apposition (synaptic size) (μm) | 0.350 ± 0.01 | 0.448 ± 0.01 + 28%$^a$ | 0.431 ± 0.01 + 23%$^a$ |
| Total synaptic contact area per unit of volume (μm$^2$/mm$^3$) | 0.365 ± 0.02 | 0.386 ± 0.01 + 5% | 0.320 ± 0.01 − 12.3%$^{b,c}$ |

There is a substantial body of evidence that inflammation causes neurodegenerative diseases in particular Alzheimer's disease (AD). Human aging is a ubiquitous complex phenomenon that results from environmental, stochastic, genetic, and epigenetic events in different cell types and tissues and their interactions throughout life. A pervasive feature of aging tissues and most if not, all age-related diseases is chronic inflammation. "Inflammaging" describes the low-grade, chronic, systemic inflammation in aging, in the absence of overt infection ("sterile" inflammation) and is a highly significant risk factor for both morbidity and mortality in the elderly people. There is overwhelming epidemiological evidence that a state of mild inflammation, revealed by elevated levels of inflammatory biomarkers such as C-reactive protein and interleukin-6 (IL-6), is associated and predictive of many aging phenotypes—for example, changes in body composition, energy production and utilization, metabolic homeostasis, immune senescence, and neuronal health. The etiology of inflammation and its potential causal role in contributing to adverse health outcomes remains largely unknown. The identification of pathways that control age-related inflammation across multiple systems is therefore important in order to understand whether treatments that modulate Inflammaging may be beneficial in old people.

It is generally known that some of the causes of most neurodegenerative diseases, as a person ages, can be arrested with antioxidants and therapeutics. However, it may not be possible to treat all causes, therefore it is necessary to adopt a strategy to regenerate and restore neurons, dendrites and synapses.

It has been recently reported by Ly et al. (Cell Rep., 2018, 23(11):3179-82), that psychedelics promote structural and functional neural plasticity. It has been reported that certain psychedelics can promote changes in neuronal structure across vertebrates (rats) and invertebrates (Drosophila) spe- cies suggesting that they act through an evolutionary conserved mechanism. It is speculated that psychedelics may be used to treat depression, but there is no discussion or suggestion about efficacy of psychedelics to treat chronic neurodegenerative diseases.

Figure 2:
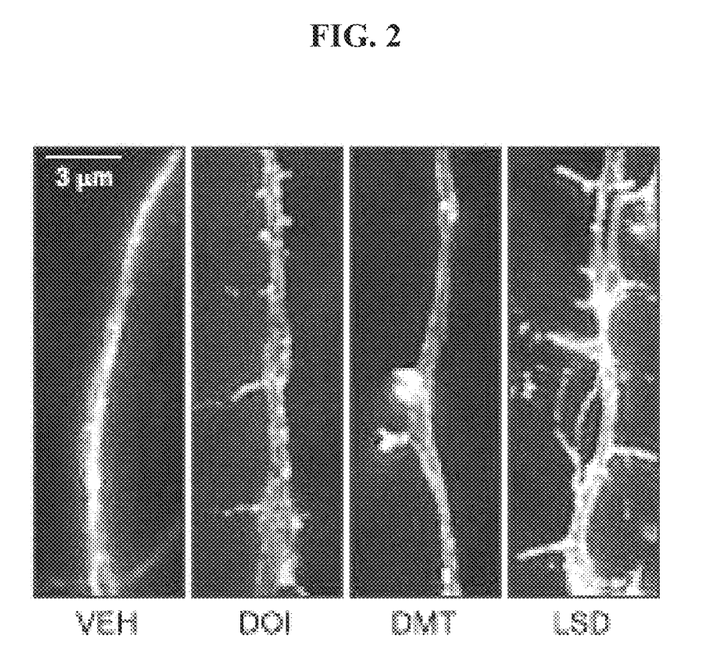
FIG. 2 shows an image sequence of cortical rat neurons, with regenerated dendrites and synaptic connections after exposure to various tryptamine small molecules.

Referring to FIG. 2, the effect of various tryptamines on rat cortical dendrite and synaptic connections after 24 hours of exposure is demonstrated. As can be seen in the image, there is a dramatic increase in neurite and synapto genesis, particularly when the subject was treated with Lysergic acid diethylamide (LSD) having the formula:

The effect is dramatic and fast even with very small doses of the compounds which is a desirable profile for a therapeutic molecule. Looking at FIG. 2 from left to right, it is apparent that LSD>DMT>DOI>Vehicle with regards to dendritic and synaptic generation. Potential therapeutics that can be used in the present invention are tryptamines such as tryptamines and phenethylamines selected from the group, N, N-dimethyltryptamine, 5-methoxy-N, N-dimethyltryptamine, Ketamine, noribogaine, psilocin 3,4-methylenedioxymethamphetamine, mescaline, psilocin, and psilocybin. The dose concentration will vary by molecule type but can range for 0.00001 to 250 milligrams to kilograms (mg/kg) of body weight with 0.01 to 50 mg/kg being preferred.

Tryptamines (also referred to herein as "tryptamine molecules), also known as serotonin analogues, are organic compounds which may be thought of as being derived from tryptamine, The molecular structures of all tryptamines contain an indole ring, joined to an amino ($NH_2$) group via an ethyl (—CH2-CH2-) sidechain. In substituted tryptamines, the indole ring, sidechain, and/or amino group are modified by substituting another group for one of the hydrogen (H) atoms. Well-known tryptamines include serotonin, an important neurotransmitter, and melatonin, a hormone involved in regulating the sleep-wake cycle. Tryptamine alkaloids are found in fungi, plants and animals; and sometimes used by humans for the neurological or psychotropic effects of the substance. Prominent examples of tryptamine alkaloids include psilocybin (from "Psilocybin mushrooms") and DMT. Many synthetic tryptamines have also been made, including the migraine drug sumatriptan, and psychedelic drugs. The tryptamine structure, in particular its indole ring, may be part of the structure of some more complex compounds, for example: LSD, ibogaine, mitragynine and yohimbine. Preferred tryptamines, capable of practicing the claimed process, include, but are not limited to, N, N-dimethyltryptamine, 5-methoxy-N, N-dimethyltryptamine, mescaline, psilocin, 3,4-methylenedioxymethamphetamine, and psilocybin.

In order to better understand how to practice the invention an example of a therapeutic recommendation for patients is given below.

Example 1. LSD is always taken orally and it is only injected for research purposes. It is commonly dissolved in blotting paper that can be broken down into tabs. Other, less common, ways of taking this psychedelic are consuming it in the form of a liquid or gelatin. The patient should place the tab under their tongue for around 10 minutes, after that, they can safely swallow the tab. The dose amount can vary by body weight and desired restorative effect, Low: 25-100 μg (people report feeling some effects with as little as 20 μg), Medium (common): 65-175 μg, High: 175-250 μg, and Heavy: 250+μg for a typical body weight of 70 Kgs. In the present invention it is recommended to keep the dose equal to or less than medium to minimize any unwanted side effects or unpleasant psychedelic experiences.

The start time below is when the patient will usually begin to feel the effects of LSD from the time when the patient first ingests it. Duration is roughly the length of time the patient will experience the effects, after which the effects will start to wind down and they might start to feel the calm-down/comedown effects. Start 30-90 minutes, peak 2-3 hours and a duration of 9-14 hours. This depends heavily on the person and her/his state. Factors such as heart rate and blood pressure or the presence of other drugs in the blood affect the time the drug will take to have an effect. A higher heart rate and blood pressure than normal would make the effects to kick in faster. This can also vary with how much the patient has taken: the higher the dose taken by the patient, the longer the effect will last. Since this is intended for chronic use the lower the dose the better to maintain optimal neurite and synapto genesis.

Based on the example above it is expected that the average number of dendritic structures and synaptic branches will double for a typical neuron thereby restoring cognitive functions such as memory and spatial recognition that may have been compromised by disease progression.

As stated previously, the claimed method may also be practiced using phenethylamines either alone or in combination with tryptamines. Phenethylamine (PEA) is an organic compound, natural monoamine alkaloid, and trace amine, which acts as a central nervous system stimulant in humans. In the brain, phenethylamine regulates monoamine neurotransmission by binding to trace amine-associated receptor 1 (TAAR1) and inhibiting vesicular monoamine transporter 2 (VMAT2) in monoamine neurons; to a lesser extent, it also acts as a neurotransmitter in the human central nervous system. The structure of phenethylamine is:

Phenethylamine is sold as a dietary supplement for purported mood and weight loss-related therapeutic benefits; however, in orally ingested phenethylamine, a significant amount is metabolized in the small intestine by monoamine oxidase B (MAO-B) and then aldehyde dehydrogenase (ALDH), which convert it to phenylacetic acid. This means that for significant concentrations to reach the brain, the dosage must be higher than for other methods of administration.

Substituted phenethylamines are a chemical class of organic compounds based upon the phenethylamine structure; the class is composed of all the derivative compounds of phenethylamine which can be formed by replacing, or substituting, one or more hydrogen atoms in the phenethylamine core structure with substituents. Many substituted phenethylamines are psychoactive drugs, which belong to a variety of different drug classes, including central nervous system stimulants (e.g., amphetamine), hallucinogens (e.g., 2,5-dimethoxy-4-methylamphetamine), entactogens (e.g., 3,4-methylenedioxyamphetamine), appetite suppressants (e.g. phentermine), nasal decongestants and bronchodilators (e.g., pseudoephedrine), antidepressants (e.g. bupropion), antiparkinson agents (e.g., selegiline), and vasopressors (e.g., ephedrine), among others. Many of these psychoactive compounds exert their pharmacological effects primarily by modulating monoamine neurotransmitter systems; however, there is no mechanism of action or biological target that is common to all members of this subclass. Numerous endogenous compounds—including hormones, monoamine neurotransmitters, and many trace amines (e.g., dopamine, norepinephrine, adrenaline, tyramine, and others)—are substituted phenethylamines. Several notable recreational drugs, such as 3,4-methylenedioxy methamphetamine (also known as MDMA or ecstasy), methamphetamine, and cathinones, are also members of the class. All of the substituted amphetamines are phenethylamines, as well. Pharmaceutical drugs that are substituted phenethylamines include phenelzine, phenformin, and fanetizole, among many others.

It may also be beneficial to supplement the method of dendritic and synaptic genesis with antioxidants that have a known effect on both brain and systemic inflammation such as Melatonin, Fisetin, Hydroxytyrosol, Carnosic Acid, Vitamin E, Vitamin C, Curcumin, Nicotinamide Mononucleotide, Tetrahydrocannabinol (THC) and Cannabidiol. The supplement dose can range from 25 to 2000 milligrams per day. An antioxidant supplement will help maintain and protect the new dendritic and synaptic formation from local inflammation.

The present invention also includes formulations used to treat neurodegenerative diseases utilizing the active agents as discussed above together with pharmaceutically acceptable carriers of said agents. The claimed formulations may also include one or more physiologically acceptable excipients. The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference. In particular, physiologically acceptable excipient, selected from the group comprising bulking agents, mixing agents, anticaking agents, aggregating agents or binders, lubricants, coating agents, stabilizers, natural flavorings, or a mixture thereof, preferably bulking agents, anticaking agents, stabilizers and natural flavorings and a mixture thereof, may be included in the claimed formulations.

Formulations as discussed herein may also contain a physiologically acceptable surfactant, buffer and/or preservative, provided said surfactant, buffer and/or preservative do not inhibit the therapeutic activity of any of the active agents. A "surfactant" as used herein is any compound that can greatly reduce the surface tension of water when used in very low concentrations. A "buffer" as used herein is any acid or salt combination which is pharmaceutically acceptable and capable of maintaining the composition of the present invention within a desired pH range. As used herein, a "preservative" is pharmaceutically acceptable, suitable for administration to a subject, which inhibits, prevents or delays the growth or microorganisms including, for example bacteria, viruses and fungi in the compositions of the present invention. Suitable preservatives for use in the compositions and methods of the present invention include, but are not limited to, cresols, benzyl alcohol, phenol, benzalkonium chloride, benzethonium chloride, chlorobutanol, phenylethyl alcohol, methyl paraben, propyl paraben, thiomersal and phenylmercuric nitrate and acetate, citric acid, sodium citrate, potassium sorbate, vitamin C (ascorbic acid), sodium ascorbate, sodium benzoate, potassium benzoate, grapefruit seed oil, or vegetable glycerin. In one embodiment, the preservative is m-cresol, chlorocresol or phenol.

Kits

This disclosure also provides kits for conveniently and effectively implementing the methods disclosed herein. Such kits comprise any subject composition, and a means for facilitating compliance with methods disclosed herein. Such kits provide a convenient and effective means for assuring that the subject to be treated takes the appropriate active in the correct dosage in the correct manner. The compliance means of such kits includes any means which facilitates administering the actives according to a method disclosed herein. Such compliance means include instructions, packaging, and dispensing means, and combinations thereof. Kit components may be packaged for either manual or partially or wholly automated practice of the foregoing methods. In other embodiments involving kits, the disclosure contemplates a kit including compositions disclosed herein, and optionally instructions for their use.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The above discussion is meant to be illustrative of the principle and various embodiments of the present invention. Numerous variations, combinations and modifications will become apparent to those skilled in the art once the above disclosure is fully appreciated. It is intended that the following claims be interpreted to embrace all such variations and modifications.

What is claimed is:

1. A formulation consisting of
one or more tryptamine molecules or pharmaceutically acceptable salts thereof, selected from the group consisting of lysergic acid diethylamide, N, N-dimethyltryptamine, 5-methoxy-N, N-dimethyltryptamine, mescaline, psilocin, and psilocybin;
one or more phenethylamine molecules, wherein said one or more phenethylamine molecules are selected from the group consisting of 3,4-methylenedioxymethamphetamine, amphetamines, 2,5-dimethoxy-4-methylamphetamine, 3,4-methylenedioxyamphetamine, phentermine, pseudoephedrine, bupropion, selegiline, ephedrine, dopamine, norepinephrine, adrenaline, tyramine, methamphetamine, cathinones, phenelzine, phenformin, fanetizole and other phenethylamine molecule belonging to hallucinogens, entactogens, anti-Parkinson agents, or vasopressors; and
one or more pharmaceutically-acceptable carrier or excipient, wherein said one or more pharmaceutically-acceptable carrier or excipient is selected from the group consisting of bulking agents, mixing agents, anticaking agents, aggregating agents, binders, lubricants, coating agents, stabilizers, natural flavorings, surfactants, buffers, and preservatives; and
one or more antioxidants, wherein said one or more antioxidants is selected from the group consisting of melatonin, fisetin, hydroxytyrosol, carnosic acid, vitamin E, vitamin C, curcumin, and nicotinamide mononucleotide;
wherein said formulation contains a sufficient amount of tryptamine molecules to treat a patient suffering from a neurodegenerative disease.

2. The formulation according to claim 1, wherein said sufficient amount of tryptamine molecules containing a dose of said one or more tryptamine molecules, or pharmaceutically acceptable is salts thereof, in an amount ranging from 25 μg to more than 250 μg;
wherein said dose in said formulation is determined by the body weight of the patient in need of treatment thereof.

3. The formulation according to claim 1, wherein said sufficient amount of tryptamine molecules containing a dose of said one or more tryptamine molecules, or pharmaceutically acceptable is salts thereof, in an amount ranging from 65 μg to 175 μg;
wherein said dose in said formulation is determined by the body weight of the patient in need of treatment thereof.

* * * * *

UNITED STATES PATENT AND TRADEMARK OFFICE
CERTIFICATE OF CORRECTION

PATENT NO. : 12,083,116 B2
APPLICATION NO. : 17/254534
DATED : September 10, 2024
INVENTOR(S) : Robert John Petcavich It is certified that error appears in the above-identified patent and that said Letters Patent is hereby corrected as shown below:

In the Specification

In Column 1, Line 45, because the reference to the nucleotide sequence should be included, this line should read "peptide (SEQ ID NO:1).".
In Column 4, Line 46, because the reference to the nucleotide sequence should be included, this line should read "C-reactive protein (SEQ ID NO: 2)";
In Column 4, Line 46, because the reference to the nucleotide sequence should be included, this line should read "interleukin-6 (IL-6) (SEQ ID NO: 3)".
In Column 6, Line 56, because the reference to the nucleotide sequence should be included, this line should read "receptor 1 (TAAR1) (SEQ ID NO: 4)";
In Column 6, Line 57, because the reference to the nucleotide sequence should be included, this line should read "transporter 2 (VMAT2) (SEQ ID NO: 5)".
In Column 7, Line 5, because the reference to the nucleotide sequence should be included, this line should read "oxidase B (MAO-B) (SEQ ID NO: 6)";
In Column 7, Line 6, because the reference to the nucleotide sequence should be included, this line should read "(ALDH) (SEQ ID NO: 7),".

Signed and Sealed this
Fifth Day of November, 2024

Katherine Kelly Vidal
*Director of the United States Patent and Trademark Office*

SEQUENCE LISTING

<160> NUMBER OF SEQ ID NOS: 7

<210> SEQ ID NO 1
<211> LENGTH: 9
<212> TYPE: PRT
<213> ORGANISM: Homo sapiens

<400> SEQUENCE: 1

Gln Lys Leu Val Phe Phe Ala Glu Asp
1               5

<210> SEQ ID NO 2
<211> LENGTH: 186
<212> TYPE: PRT
<213> ORGANISM: Homo sapiens

<400> SEQUENCE: 2

Thr Asp Met Ser Arg Lys Ala Phe Val Phe Pro Lys Glu Ser Asp Thr
1               5                   10                  15

Ser Tyr Val Ser Leu Lys Ala Pro Leu Thr Lys Pro Leu Lys Ala Phe
                20                  25                  30

Thr Val Cys Leu His Phe Tyr Thr Glu Leu Ser Ser Thr Arg Gly Tyr
            35                  40                  45

Ser Ile Phe Ser Tyr Ala Thr Lys Arg Gln Asp Asn Glu Ile Leu Phe
    50                  55                  60

Glu Val Pro Glu Val Thr Val Ala Pro Val His Ile Cys Thr Ser Trp
65                  70                  75                  80

Glu Ser Ala Ser Gly Ile Val Glu Phe Trp Val Asp Gly Lys Pro Arg
                85                  90                  95

Val Arg Lys Ser Leu Lys Lys Gly Tyr Thr Val Gly Ala Glu Ala Ser
                100                 105                 110

Ile Ile Leu Gly Gln Glu Gln Asp Ser Phe Gly Gly Asn Phe Glu Gly
            115                 120                 125

Ser Gln Ser Leu Val Gly Asp Ile Gly Asn Val Asn Met Trp Asp Phe
    130                 135                 140

Val Leu Ser Pro Asp Glu Ile Asn Thr Ile Tyr Leu Gly Gly Pro Phe
145                 150                 155                 160

Ser Pro Asn Val Leu Asn Trp Arg Ala Leu Lys Tyr Glu Val Gln Gly
                165                 170                 175

Glu Val Phe Thr Lys Pro Gln Leu Trp Pro
                180                 185

<210> SEQ ID NO 3
<211> LENGTH: 212
<212> TYPE: PRT
<213> ORGANISM: Homo sapiens

<400> SEQUENCE: 3

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

```
Ser Lys Glu Ala Leu Ala Glu Asn Asn Leu Asn Leu Pro Lys Met Ala
            85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Gln Ala Arg Ala Val Gln
            130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 4
<211> LENGTH: 339
<212> TYPE: PRT
<213> ORGANISM: Homo sapiens

<400> SEQUENCE: 4

Met Met Pro Phe Cys His Asn Ile Ile Asn Ile Ser Cys Val Lys Asn
1               5                   10                  15

Asn Trp Ser Asn Asp Val Arg Ala Ser Leu Tyr Ser Leu Met Val Leu
            20                  25                  30

Ile Ile Leu Thr Thr Leu Val Gly Asn Leu Ile Val Ile Val Ser Ile
            35                  40                  45

Ser His Phe Lys Gln Leu His Thr Pro Thr Asn Trp Leu Ile His Ser
    50                  55                  60

Met Ala Thr Val Asp Phe Leu Leu Gly Cys Leu Val Met Pro Tyr Ser
65                  70                  75                  80

Met Val Arg Ser Ala Glu His Cys Trp Tyr Phe Gly Glu Val Phe Cys
            85                  90                  95

Lys Ile His Thr Ser Thr Asp Ile Met Leu Ser Ser Ala Ser Ile Phe
            100                 105                 110

His Leu Ser Phe Ile Ser Ile Asp Arg Tyr Tyr Ala Val Cys Asp Pro
            115                 120                 125

Leu Arg Tyr Lys Ala Lys Met Asn Ile Leu Val Ile Cys Val Met Ile
            130                 135                 140

Phe Ile Ser Trp Ser Val Pro Ala Val Phe Ala Phe Gly Met Ile Phe
145                 150                 155                 160

Leu Glu Leu Asn Phe Lys Gly Ala Glu Glu Ile Tyr Tyr Lys His Val
            165                 170                 175

His Cys Arg Gly Gly Cys Ser Val Phe Phe Ser Lys Ile Ser Gly Val
            180                 185                 190

Leu Thr Phe Met Thr Ser Phe Tyr Ile Pro Gly Ser Ile Met Leu Cys
            195                 200                 205

Val Tyr Tyr Arg Ile Tyr Leu Ile Ala Lys Glu Gln Ala Arg Leu Ile
            210                 215                 220

Ser Asp Ala Asn Gln Lys Leu Gln Ile Gly Leu Glu Met Lys Asn Gly
```

```
                225                 230                 235                 240
Ile Ser Gln Ser Lys Glu Arg Lys Ala Val Lys Thr Leu Gly Ile Val
                    245                 250                 255

Met Gly Val Phe Leu Ile Cys Trp Cys Pro Phe Phe Ile Cys Thr Val
                    260                 265                 270

Met Asp Pro Phe Leu His Tyr Ile Ile Pro Pro Thr Leu Asn Asp Val
                    275                 280                 285

Leu Ile Trp Phe Gly Tyr Leu Asn Ser Thr Phe Asn Pro Met Val Tyr
                    290                 295                 300

Ala Phe Phe Tyr Pro Trp Phe Arg Lys Ala Leu Lys Met Met Leu Phe
305                 310                 315                 320

Gly Lys Ile Phe Gln Lys Asp Ser Ser Arg Cys Lys Leu Phe Leu Glu
                    325                 330                 335

Leu Ser Ser

<210> SEQ ID NO 5
<211> LENGTH: 514
<212> TYPE: PRT
<213> ORGANISM: Homo sapiens

<400> SEQUENCE: 5

Met Ala Leu Ser Glu Leu Ala Leu Val Arg Trp Leu Gln Glu Ser Arg
1               5                   10                  15

Arg Ser Arg Lys Leu Ile Leu Phe Ile Val Phe Leu Ala Leu Leu Leu
                    20                  25                  30

Asp Asn Met Leu Leu Thr Val Val Val Pro Ile Ile Pro Ser Tyr Leu
                    35                  40                  45

Tyr Ser Ile Lys His Glu Lys Asn Ala Thr Glu Ile Gln Thr Ala Arg
            50                  55                  60

Pro Val His Thr Ala Ser Ile Ser Asp Ser Phe Gln Ser Ile Phe Ser
65              70                  75                  80

Tyr Tyr Asp Asn Ser Thr Met Val Thr Gly Asn Ala Thr Arg Asp Leu
                85                  90                  95

Thr Leu His Gln Thr Ala Thr Gln His Met Val Thr Asn Ala Ser Ala
                    100                 105                 110

Val Pro Ser Asp Cys Pro Ser Glu Asp Lys Asp Leu Leu Asn Glu Asn
                    115                 120                 125

Val Gln Val Gly Leu Leu Phe Ala Ser Lys Ala Thr Val Gln Leu Ile
            130                 135                 140

Thr Asn Pro Phe Ile Gly Leu Leu Thr Asn Arg Ile Gly Tyr Pro Ile
145                 150                 155                 160

Pro Ile Phe Ala Gly Phe Cys Ile Met Phe Val Ser Thr Ile Met Phe
                    165                 170                 175

Ala Phe Ser Ser Ser Tyr Ala Phe Leu Leu Ile Ala Arg Ser Leu Gln
                    180                 185                 190

Gly Ile Gly Ser Ser Cys Ser Ser Val Ala Gly Met Gly Met Leu Ala
            195                 200                 205

Ser Val Tyr Thr Asp Asp Glu Glu Arg Gly Asn Val Met Gly Ile Ala
        210                 215                 220

Leu Gly Gly Leu Ala Met Gly Val Leu Val Gly Pro Pro Phe Gly Ser
225                 230                 235                 240

Val Leu Tyr Glu Phe Val Gly Lys Thr Ala Pro Phe Leu Val Leu Ala
                    245                 250                 255

Ala Leu Val Leu Leu Asp Gly Ala Ile Gln Leu Phe Val Leu Gln Pro
```

```
                    260                 265                 270
Ser Arg Val Gln Pro Glu Ser Gln Lys Gly Thr Pro Leu Thr Thr Leu
            275                 280                 285

Leu Lys Asp Pro Tyr Ile Leu Ile Ala Ala Gly Ser Ile Cys Phe Ala
            290                 295                 300

Asn Met Gly Ile Ala Met Leu Glu Pro Ala Leu Pro Ile Trp Met Met
305                 310                 315                 320

Glu Thr Met Cys Ser Arg Lys Trp Gln Leu Gly Val Ala Phe Leu Pro
            325                 330                 335

Ala Ser Ile Ser Tyr Leu Ile Gly Thr Asn Ile Phe Gly Ile Leu Ala
            340                 345                 350

His Lys Met Gly Arg Trp Leu Cys Ala Leu Leu Gly Met Ile Ile Val
            355                 360                 365

Gly Val Ser Ile Leu Cys Ile Pro Phe Ala Lys Asn Ile Tyr Gly Leu
            370                 375                 380

Ile Ala Pro Asn Phe Gly Val Gly Phe Ala Ile Gly Met Val Asp Ser
385                 390                 395                 400

Ser Met Met Pro Ile Met Gly Tyr Leu Val Asp Leu Arg His Val Ser
                405                 410                 415

Val Tyr Gly Ser Val Tyr Ala Ile Ala Asp Val Ala Phe Cys Met Gly
            420                 425                 430

Tyr Ala Ile Gly Pro Ser Ala Gly Ala Ile Ala Lys Ala Ile Gly
            435                 440                 445

Phe Pro Trp Leu Met Thr Ile Ile Gly Ile Ile Asp Ile Leu Phe Ala
450                 455                 460

Pro Leu Cys Phe Phe Leu Arg Ser Pro Ala Lys Glu Glu Lys Met
465                 470                 475                 480

Ala Ile Leu Met Asp His Asn Cys Pro Ile Lys Thr Lys Met Tyr Thr
                485                 490                 495

Gln Asn Asn Ile Gln Ser Tyr Pro Ile Gly Glu Asp Glu Glu Ser Glu
                500                 505                 510

Ser Asp

<210> SEQ ID NO 6
<211> LENGTH: 520
<212> TYPE: PRT
<213> ORGANISM: Homo sapiens

<400> SEQUENCE: 6

Met Ser Asn Lys Cys Asp Val Val Val Gly Gly Ile Ser Gly
1               5                   10                  15

Met Ala Ala Ala Lys Leu Leu His Asp Ser Gly Leu Asn Val Val
                20                  25                  30

Leu Glu Ala Arg Asp Arg Val Gly Gly Arg Thr Tyr Thr Leu Arg Asn
            35                  40                  45

Gln Lys Val Lys Tyr Val Asp Leu Gly Gly Ser Tyr Val Gly Pro Thr
    50                  55                  60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                85                  90                  95

Tyr Pro Phe Arg Gly Pro Phe Pro Pro Val Trp Asn Pro Ile Thr Tyr
            100                 105                 110

Leu Asp His Asn Asn Phe Trp Arg Thr Met Asp Asp Met Gly Arg Glu
```

```
            115                 120                 125
Ile Pro Ser Asp Ala Pro Trp Lys Ala Pro Leu Ala Glu Glu Trp Asp
    130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
            180                 185                 190

Gly Gly Thr Thr Arg Ile Ile Ser Thr Thr Asn Gly Gly Gln Glu Arg
        195                 200                 205

Lys Phe Val Gly Gly Ser Gly Gln Val Ser Glu Arg Ile Met Asp Leu
    210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
            260                 265                 270

His Phe Asn Pro Pro Leu Pro Met Met Arg Asn Gln Met Ile Thr Arg
        275                 280                 285

Val Pro Leu Gly Ser Val Ile Lys Cys Ile Val Tyr Tyr Lys Glu Pro
    290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
            340                 345                 350

Ala Arg Leu Thr Lys Glu Glu Arg Leu Lys Lys Leu Cys Glu Leu Tyr
        355                 360                 365

Ala Lys Val Leu Gly Ser Leu Glu Ala Leu Glu Pro Val His Tyr Glu
    370                 375                 380

Glu Lys Asn Trp Cys Glu Glu Gln Tyr Ser Gly Gly Cys Tyr Thr Thr
385                 390                 395                 400

Tyr Phe Pro Pro Gly Ile Leu Thr Gln Tyr Gly Arg Val Leu Arg Gln
                405                 410                 415

Pro Val Asp Arg Ile Tyr Phe Ala Gly Thr Glu Thr Ala Thr His Trp
            420                 425                 430

Ser Gly Tyr Met Glu Gly Ala Val Glu Ala Gly Glu Arg Ala Ala Arg
        435                 440                 445

Glu Ile Leu His Ala Met Gly Lys Ile Pro Glu Asp Glu Ile Trp Gln
    450                 455                 460

Ser Glu Pro Glu Ser Val Asp Val Pro Ala Gln Pro Ile Thr Thr Thr
465                 470                 475                 480

Phe Leu Glu Arg His Leu Pro Ser Val Pro Gly Leu Leu Arg Leu Ile
                485                 490                 495

Gly Leu Thr Thr Ile Phe Ser Ala Thr Ala Leu Gly Phe Leu Ala His
            500                 505                 510

Lys Arg Gly Leu Leu Val Arg Val
        515                 520

<210> SEQ ID NO 7
```

<211> LENGTH: 517
<212> TYPE: PRT
<213> ORGANISM: Homo sapiens

<400> SEQUENCE: 7

```
Met Leu Arg Ala Ala Arg Phe Gly Pro Arg Leu Gly Arg Arg Leu
1               5                   10                  15

Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
                35                  40                  45

Val Ser Arg Lys Thr Phe Pro Thr Val Asn Pro Ser Thr Gly Glu Val
50                  55                  60

Ile Cys Gln Val Ala Glu Gly Asp Lys Glu Asp Val Asp Lys Ala Val
65                  70                  75                  80

Lys Ala Ala Arg Ala Ala Phe Gln Leu Gly Ser Pro Trp Arg Arg Met
                85                  90                  95

Asp Ala Ser His Arg Gly Arg Leu Leu Asn Arg Leu Ala Asp Leu Ile
                100                 105                 110

Glu Arg Asp Arg Thr Tyr Leu Ala Ala Leu Glu Thr Leu Asp Asn Gly
            115                 120                 125

Lys Pro Tyr Val Ile Ser Tyr Leu Val Asp Leu Asp Met Val Leu Lys
            130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
                180                 185                 190

Ala Trp Lys Leu Gly Pro Ala Leu Ala Thr Gly Asn Val Val Val Met
            195                 200                 205

Lys Val Ala Glu Gln Thr Pro Leu Thr Ala Leu Tyr Val Ala Asn Leu
210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
                260                 265                 270

Ala Ala Gly Ser Ser Asn Leu Lys Arg Val Thr Leu Glu Leu Gly Gly
            275                 280                 285

Lys Ser Pro Asn Ile Ile Met Ser Asp Ala Asp Met Asp Trp Ala Val
290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
            355                 360                 365

Lys Ile Leu Gly Tyr Ile Asn Thr Gly Lys Gln Glu Gly Ala Lys Leu
370                 375                 380

Leu Cys Gly Gly Gly Ile Ala Ala Asp Arg Gly Tyr Phe Ile Gln Pro
```

-continued

| | 385 | | | | 390 | | | | 395 | | | | 400 | |
|---|---|---|---|---|---|---|---|---|---|---|---|---|---|---|
| Thr | Val | Phe | Gly | Asp 405 | Val | Gln | Asp | Gly | Met 410 | Thr | Ile | Ala | Lys 415 | Glu | Glu |
| Ile | Phe | Gly | Pro 420 | Val | Met | Gln | Ile | Leu 425 | Lys | Phe | Lys | Thr | Ile 430 | Glu | Glu |
| Val | Val | Gly 435 | Arg | Ala | Asn | Asn | Ser 440 | Thr | Tyr | Gly | Leu | Ala 445 | Ala | Ala | Val |
| Phe | Thr 450 | Lys | Asp | Leu | Asp | Lys 455 | Ala | Asn | Tyr | Leu | Ser 460 | Gln | Ala | Leu | Gln |
| Ala 465 | Gly | Thr | Val | Trp | Val 470 | Asn | Cys | Tyr | Asp | Val 475 | Phe | Gly | Ala | Gln | Ser 480 |
| Pro | Phe | Gly | Gly | Tyr 485 | Lys | Met | Ser | Gly | Ser 490 | Gly | Arg | Glu | Leu | Gly 495 | Glu |
| Tyr | Gly | Leu | Gln 500 | Ala | Tyr | Thr | Glu | Val 505 | Lys | Thr | Val | Thr | Val 510 | Lys | Val |
| Pro | Gln | Lys 515 | Asn | Ser | | | | | | | | | | | |